US011759122B1

(12) United States Patent
Ahmad

(10) Patent No.: US 11,759,122 B1
(45) Date of Patent: Sep. 19, 2023

(54) BREATH ANALYSIS SYSTEM WITH PREDICTIVE SENSOR PREPARATION

(71) Applicant: Invoy Holdings Inc., Irvine, CA (US)

(72) Inventor: Lubna M. Ahmad, Irvine, CA (US)

(73) Assignee: Invoy Holdings Inc., Irvine, CA (US)

( * ) Notice: Subject to any disclaimer, the term of this patent is extended or adjusted under 35 U.S.C. 154(b) by 0 days.

(21) Appl. No.: 17/810,897

(22) Filed: Jul. 6, 2022

(51) Int. Cl.
| | |
|---|---|
| A61B 5/00 | (2006.01) |
| A61B 5/08 | (2006.01) |
| A61B 5/0205 | (2006.01) |
| A61B 5/097 | (2006.01) |
| G16H 40/67 | (2018.01) |
| G16H 10/40 | (2018.01) |
| A61B 5/024 | (2006.01) |

(52) U.S. Cl.
CPC ............ A61B 5/082 (2013.01); A61B 5/0002 (2013.01); A61B 5/0205 (2013.01); A61B 5/097 (2013.01); G16H 10/40 (2018.01); G16H 40/67 (2018.01); A61B 5/02438 (2013.01); A61B 2560/0209 (2013.01); A61B 2560/0431 (2013.01)

(58) Field of Classification Search
CPC ............................... A61B 5/082; A61B 5/002
USPC .................................................. 600/300–301
See application file for complete search history.

(56) References Cited

U.S. PATENT DOCUMENTS

| | | | |
|---|---|---|---|
| 9,341,632 B1 | 5/2016 | Ahmad et al. | |
| 10,068,484 B2 | 9/2018 | Ahmad et al. | |
| 10,782,284 B1* | 9/2020 | Ahmad | G01N 21/314 |
| 11,250,942 B1 | 2/2022 | Ahmad et al. | |
| 2007/0016092 A1* | 1/2007 | Shaw | A61B 5/097 |
| | | | 600/532 |
| 2016/0150995 A1 | 6/2016 | Ratto et al. | |
| 2016/0187279 A1 | 6/2016 | Tayebi et al. | |
| 2016/0371590 A1* | 12/2016 | Blackley | G01N 33/497 |
| 2019/0231222 A1* | 8/2019 | Ahmad | A61B 5/091 |
| 2020/0268278 A1 | 8/2020 | Ratto et al. | |

\* cited by examiner

*Primary Examiner* — Nicole F Lavert
*Assistant Examiner* — Nicole F Johnson
(74) *Attorney, Agent, or Firm* — Knobbe, Martens, Olson & Bear, LLP

(57) ABSTRACT

A breath analysis system comprises a breath analysis device having a semiconductor sensor, such as a metal oxide semiconductor sensor, that needs to be heated or otherwise prepared before a breath test can be performed. To reduce or avoid a user-perceived delay (typically multiple minutes) associated with the sensor preparation operation, the system predictively initiates a sensor preparation operation based on a determination or prediction of whether the user is in an adequate state to perform a breath test. This prediction may be based on one or more factors, such as the current time, whether the breath analysis device is within wireless communication (e.g., Bluetooth) range of the user's smartphone, data reflective of the user's location and/or activity, etc.

27 Claims, 4 Drawing Sheets

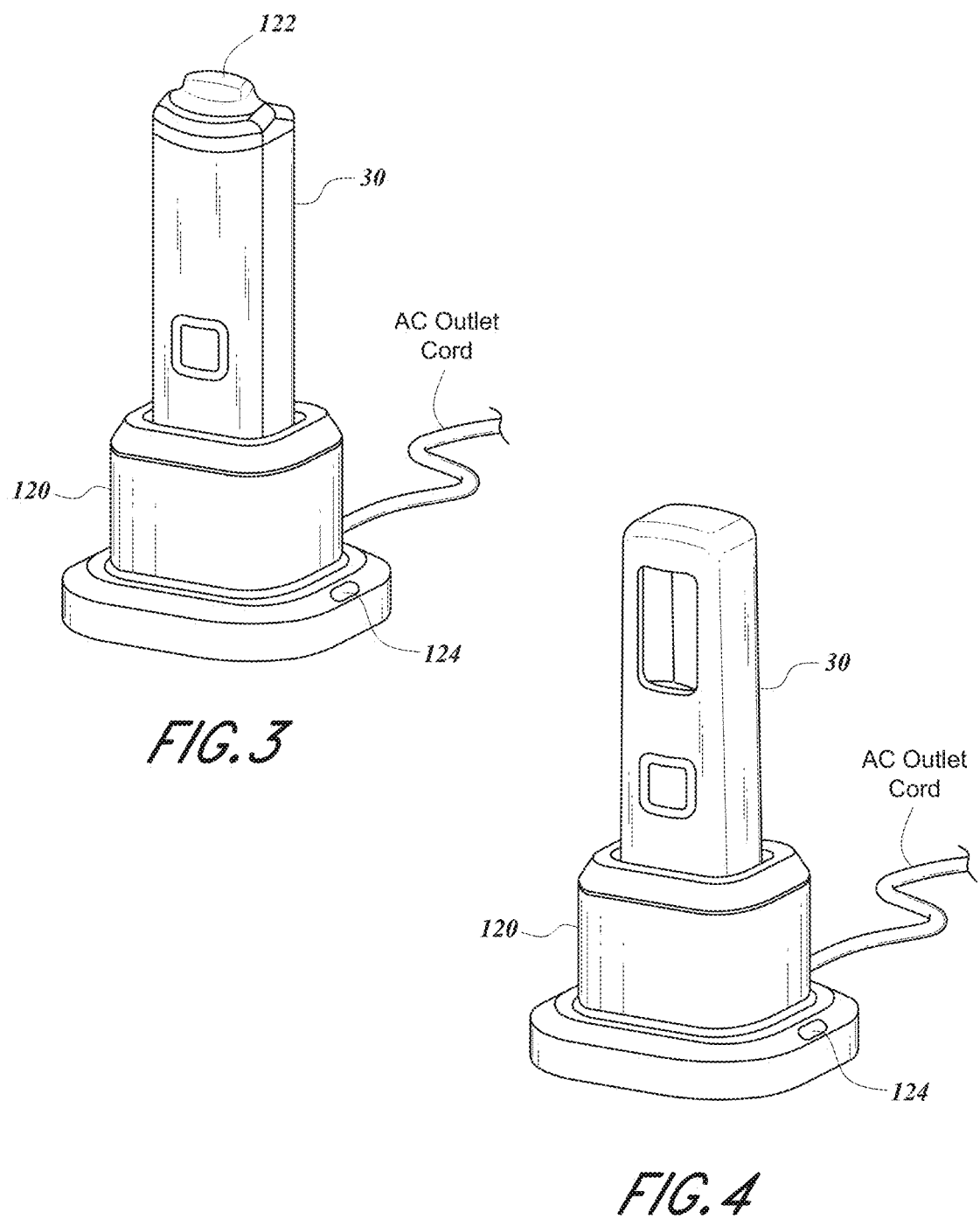

BREATH ANALYSIS SYSTEM WITH PREDICTIVE SENSOR PREPARATION

BACKGROUND OF THE INVENTION

Exhaled breath contains a variety of analytes that are useful for monitoring various physiologic conditions. For example, acetone and carbon dioxide are useful for monitoring fat metabolism and physical activity, and methane and hydrogen are useful for detecting various digestive disorders.

A variety of handheld breath analysis devices exist for enabling individuals to monitor the concentrations of these and other breath analytes. Typically, the breath analysis device measures the analyte in question using a metal oxide semiconductor (MOS) sensor that measures a resistance change of a metal oxide caused by gas absorption. Before such semiconductor sensors can generate accurate breath analyte measurements, they typically must be heated to a specified temperature.

BRIEF DESCRIPTION OF THE DRAWINGS

FIG. 3 illustrates a breath analysis device inserted into a docking cradle.

FIG. 4 illustrates the breath analysis device and docking cradle of FIG. 3, but with the breath analysis device inserted with an orientation for sterilizing the mouthpiece.

DETAILED DESCRIPTION OF THE PREFERRED EMBODIMENTS

Figure 1:
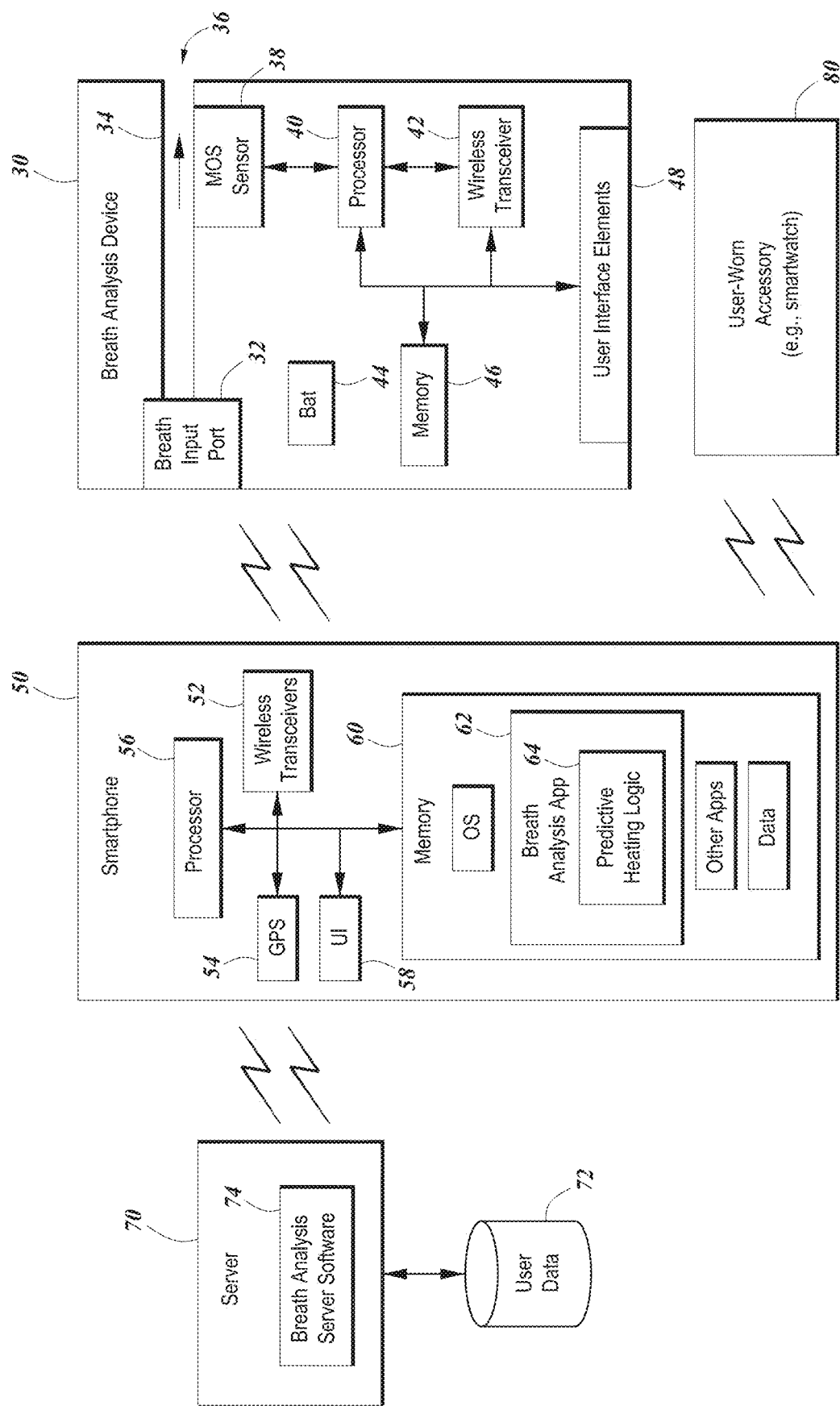
FIG. 1 illustrates a breath analysis system according to one embodiment.

One problem with existing breath analysis devices that use semiconductor sensors is that they typically have long sensor preparation times. For example, some commercially available breath analysis devices take several minutes to complete the sensor heating cycle once the device is turned on. This delay can be burdensome for users, especially if the user is expected to perform a breath test multiple times per day. In some breath analysis devices, delay can also be introduced by other types of sensor or device preparation tasks, such as the execution of a flush cycle in which air is pumped through the device.

To address this problem, the present disclosure provides a system that predictively initiates the breath analysis device's sensor heating cycle, and/or other preparation cycle, in anticipation of the user being ready to perform a breath test. The user-perceived delay associated with the heating or other preparation operation(s) is thereby avoided or significantly reduced. Preferably the system determines whether/when to initiate the sensor heating (and/or other preparation) operation based on predictions that the associated user is in an adequate state for performing a breath test.

In embodiments in which the breath analysis device operates in conjunction with a mobile application, such as a smartphone application, the predictions may, for example, be based on one or more types of data collected by the user's smartphone or other mobile device. For example, the predictions may be based on sensor data reflective of one or more of the following: (a) whether the user is awake, (b) the proximity of the user's smartphone to the breath analysis device, (c) the user's location, (d) the user's heart rate, (e) whether the user is moving at more than a threshold rate, (f) whether a voice call is in progress on the smartphone. The predictions may additionally or alternatively be based on the time of day (e.g., the current time relative to the time of day when the user ordinarily performs, or is scheduled to perform, a breath test), and/or on various triggering events (e.g., the user returns home or wakes up in the morning, a light switch is turned on in a particular room, etc.).

In some embodiments, the predictions are made programmatically by a mobile application running on the user's smartphone (or other mobile device) during defined time windows, such as a time window when the user is supposed to, or predicted to want to, perform a breath test. The time windows may, for example, be pre-specified by the user or a health coach (e.g., between 6 AM and 9 AM daily), or may be learned by the system based on the user's usage patterns. The predictions may alternatively be made in whole or in part by the breath analysis device, a docking station for the breath analysis device, a server, or some other processing/computing node.

If a predictive determination is made that the user is in an adequate state for performing a breath test, the system may preemptively cause the breath analysis device to perform a sensor heating cycle (and/or any other type of sensor preparation task that ordinarily introduces user-perceived delay) in which the device's semiconductor sensor is partially or fully heated to the necessary temperature for performing a breath test. The user thus need not take any action to initiate the sensor heating or preparation operation. Once the sensor heating operation is complete, an appropriate message may be presented to the user prompting the user to perform a breath test. The user may then immediately (or with significantly reduced delay) perform the breath test. The user-perceived delay associated with the sensor heating or preparation time is thus avoided or significantly reduced.

To implement the above-described functionality, in some embodiments the breath analysis device may be designed or configured to periodically wake up from a low power state to listen for communications from the user's smartphone, such as an instruction to perform a sensor heating cycle. For example, at the beginning of each time window in which the user is supposed to perform a breath test, the breath analysis device may enter into a state in which its wireless transceiver periodically wakes up to listen for communications. The duty cycle for waking up may be sufficiently low such that minimal battery power is consumed. In other embodiments, the logic for determining whether to preemptively initiate the sensor heating or preparation operation is implemented within the breath analysis device.

FIG. 1 illustrates a breath analysis system according to one embodiment. The system includes a battery-powered breath analysis device 30 capable of measuring the concentration of one or more analytes in the breath of a human subject or "user." The breath analysis device 30 is typically a handheld device that is small enough to be carried in the pocket of the user. The system also includes a smartphone 50 that communicates wirelessly with the breath analysis device 30. In some embodiments, the smartphone 50 may be replaced with another type of mobile computing device, such as a tablet computing device or a smartwatch, or may be omitted. As explained below, the smartphone 50 preferably runs application software that, among other things, determines when to instruct the breath analysis device 30 to preemptively perform a sensor heating operation. As discussed below, in other embodiments the logic for determining when to perform the sensor heating operation is implemented within the breath analysis device 30.

The breath analysis device 30 includes a breath input port 32 for receiving a breath sample of the user. The breath input port 32 preferably comprises a mouthpiece into which the user exhales the breath sample. In other embodiments, the user may alternatively exhale the breath sample into a breath container, such as a breath bag, that attaches to the breath input port 32, in which case the breath analysis device 30 may include a pump that extracts the breath sample from the breath container.

The breath analysis device 30 also includes a flow path 34, such as a conduit, that extends between the breath input port 32 and an exhaust port 36. The flow path 34 may, in some embodiments, include one or more valves (not shown) for controlling the flow of the breath sample and/or one or more chambers (not shown) for capturing a desired portion of the breath sample. A semiconductor sensor, which is preferably a metal oxide semiconductor (MOS) sensor 38, is positioned along the flow path 34 to measure the concentration of an analyte, such as acetone, carbon dioxide, methane or hydrogen, in the breath sample as it flows along the flow path. (As used herein, "semiconductor sensor" or "semiconductor analyte sensor" encompasses nanoparticle sensors, MOS sensors, and solid state sensors capable of detecting an analyte.) In some implementations, the MOS sensor 38 (or other type of semiconductor sensor) may be capable of, and used for, measuring the concentrations of multiple respective analytes. In addition, in some embodiments, multiple MOS sensors may be provided along the flow path 34 to measure the concentrations of different respective analytes. Where multiple such MOS sensors are present, the predictive process described herein may be used to initiate the concurrent heating of all such sensors.

The breath analysis device 30 also includes a hardware processor 40 (e.g., a microcontroller), a wireless transceiver 42, a battery 44, a memory 46, and one or more user interface elements 48. The wireless transceiver 42 is preferably a Bluetooth transceiver, such as a Bluetooth Low Energy (BLE) transceiver but may alternatively be another type of transceiver such as a WIFI transceiver. The user interface elements 48 may, for example, include one or more buttons for turning the breath analysis device on and off and for initiating a breath test. In addition, the user interface elements 48 may include a display, a sound generator, and/or a haptic signal generator, for outputting information and signals to the user, as is common among commercially available breath analysis devices. Although not shown in FIG. 1, the breath analysis device 30 may also include a pump arranged to pump air along the flow path; such a pump may be used to perform a flush operation before or after a user performs a breath test.

The memory 46 stores modules of program instructions (firmware) that are executed by the processor 40, including modules for controlling such tasks as communicating with the smartphone 50 (in embodiments in which a smartphone is used), heating the sensor 38 (and/or performing other sensor or device preparation tasks such as a flush operation), processing data received from the sensor 38, processing user input, and outputting signals and information to the user. In some cases, the memory 46 also stores program instructions that cause the breath analysis device 30 to automatically (without user input) switch between a low power or "inactive" state in which it cannot receive wireless communications and an active state in which it listens for wireless transmissions. As explained below, the breath analysis device 30 may periodically transition between these two states according to a duty cycle that maintains the breath analysis device 30 in the low power state most of the time (e.g., at least 70, 80 or 90 percent of the time).

One example of the physical configuration of the breath analysis device 30 is shown in FIGS. 3 and 4. In this particular example, the breath analysis device 30 is designed to be placed into a docking station or cradle 120 that recharges the battery 44 of the breath analysis device. The docking station or cradle may alternatively be omitted, in which case the breath analysis device 30 may be charged via a charging cable or may use a non-rechargeable battery. The embodiment of FIGS. 3 and 4 is described further below.

Referring again to FIG. 1, as is conventional, the smartphone 50 includes wireless transceivers 52 (e.g., Bluetooth, WIFI and cellular transceivers), a GPS (Global Positioning System) chip 54, a processor 56, various user interface (UI) elements 58 (e.g., a touch display, a speaker, a microphone, a haptic signal generator, etc.) and a non-volatile memory 60. The memory 60 stores, among other elements, the various mobile applications (apps) installed on the smartphone 50, including a breath analysis application 62 that communicates with the breath analysis device 30. The breath analysis application 62 may include user interfaces and associated functionality for enabling the user to perform such tasks as setting up an account with a health monitoring/coaching service provider, initiating a breath test, reviewing and interpreting breath test results, logging meals and other activities, specifying configuration options (such as time windows for performing breath tests), communicating with a human health coach, etc. The memory 60 also stores operating system (OS) code and data.

As shown in FIG. 1, the breath analysis application 62 may optionally communicate over a network with an associated physical server 70. The server 70 may run breath analysis server software 74, such as software for hosting a web portal through which health coaches or advisors can interact with users of the breath analysis devices 30. The server 70 may maintain various types of user data (e.g., account data, user profiles, analyte measurements, etc.) in a database 72. The breath analysis server software 74 may also include components for providing automated health coaching to users, as described in U.S. Pat. No. 11,170,662, the disclosure of which is hereby incorporated by reference.

In addition, the smartphone 50 may optionally communicate wirelessly with a user-worn accessory 80, such as a smartwatch, a wrist-worn fitness tracker, a sleep monitoring device, a continuous glucose monitor or a continuous ketone monitor, that collects and transmits to the smartphone 50 various types of data regarding the physiologic state and activity of the user, such as heart rate data, motion data, skin temperature, oxygen saturation, breathing rate, sleep state, blood glucose level or blood ketone level. As explained below, where such types of data are available, some or all such data may be used to assess whether the user is in an adequate state to perform a breath test.

Figure 2:
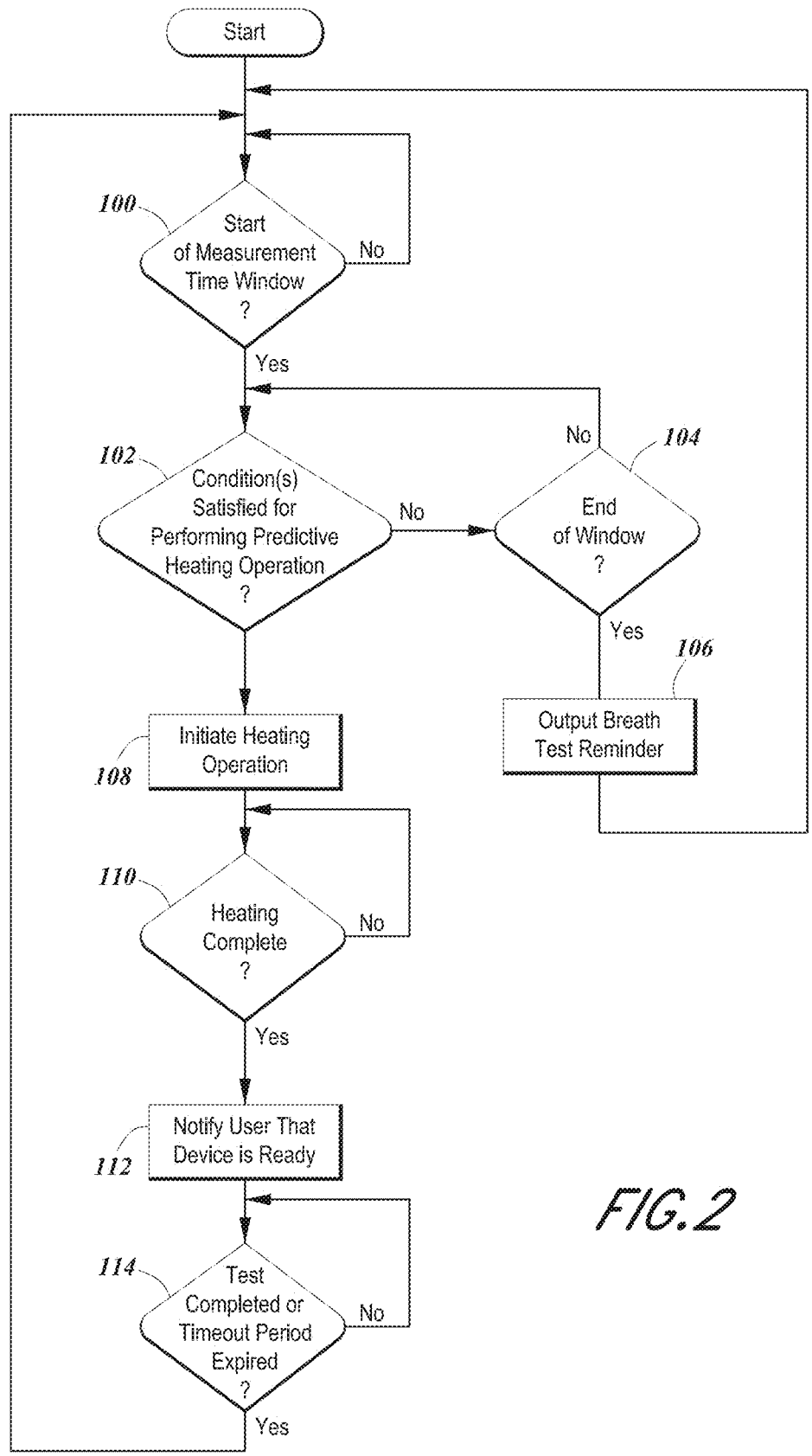
FIG. 2 illustrates one embodiment of a process for predictively initiating a sensor heating operation in the system of FIG. 1.

As further shown in FIG. 1, the breath analysis application 62 includes predictive heating logic 64 for determining when to predictively or preemptively initiate a sensor heating operation (and/or other device preparation operation). This logic 64, which may be embodied in executable program code, may alternatively be implemented partly or wholly within the breath analysis server software 74, the breath analysis device 30, a docking station for the breath analysis device 30, or on some other processing node or device. One example of this logic is shown in FIG. 2, which is discussed below.

In operation, the user initially uses the breath analysis application 62 to pair the breath analysis device 30 with the smartphone 50. The user may also be prompted via the app 62 to create a user profile and to specify one or more configuration options. As one example, in some embodiments, the user can specify one or more daily time windows for performing a breath test. The time window or windows may alternatively be configured by a health coach, learned based on usage patterns, or omitted.

In one embodiment, the breath analysis device 30, when not in active use, periodically turns on its wireless transceiver 42 (e.g., once per second, once every 5 seconds, once per minute, or at some other rate) and attempts to establish a wireless (e.g., Bluetooth or BLE) link with the smartphone 50. If no link is established, or a link is established and the smartphone instructs the breath analysis device that no action is required, the breath analysis device 30 turns off its wireless transceiver 42 to effectively enter back into a low-power or "sleep" state. Preferably, the breath analysis device 30 uses a duty cycle in which the wireless transceiver 42 is off at least 70% of the time, and more preferably at least 80% or at least 90% of the time. This reduces the drain on the battery 44. To further reduce battery drain, the breath analysis device 30 may keep its wireless transceiver 42 turned off when not in a defined window for performing a breath test. In some embodiments, the wireless transceiver 42 may instead be kept on.

When the breath analysis application 62 determines that a sensor heating operation should be performed, it waits for the next wireless link to be established (if no such link is currently established) and then uses the link to instruct the breath analysis device 30 to perform a sensor heating operation. Thus, the sensor heating operation is initiated without the need for the user to interact with (e.g., turn on) the breath analysis device 30 or take any other action. To perform the sensor heating operation, the breath analysis device 30 supplies power from the battery 44 to a heating element of the MOS sensor 38 until the sensor reaches a predefined temperature or temperature range. This process usually takes more than one minute, and frequently takes several minutes (depending on the parameters of the MOS sensor, the size of the battery 44, the starting temperature of the MOS sensor, the target temperature, and other factors). In some embodiments, the sensor heating operation may involve heating the sensor 38 to a first temperature (e.g., in the range of 200 to 500 C) sufficient to burn off any absorbed chemicals and then bringing the sensor to a second, lower temperature (e.g., in the range of 150 C to 350 C) that is appropriate for performing the breath test, as described in U.S. Patent Pub. 2020/0268278, the disclosure of which is hereby incorporated by reference for purposes of disclosing examples of tasks that may be performed by a breath analysis device to prepare its sensor(s) for use.

In some embodiments, one or more additional tasks may be performed as part of, or concurrently with, the sensor heating operation. For example, in embodiments in which the breath analysis device 30 includes a pump, the pump may be activated during the sensor heating operation to perform a flush cycle, as is known in the art. Thus, although this disclosure focusses primarily on sensor heating, the process is also applicable to other tasks that may be performed in preparing a sensor or breath analysis device for use.

Once the heating operation is complete, the breath analysis device 30 notifies the breath analysis app 62 via the established wireless link, and the breath analysis app 62 generates a notification to notify the user that the breath analysis device 30 is ready for use. In some implementations, this notification may prompt the user to indicate whether they wish to proceed with the breath test, in which case a negative response from the user may cause the app 62 to instruct the breath analysis device 30 not to maintain the sensor 38 in the heated state. The breath analysis device 30 may also allow the sensor 38 to cool if the user does not perform the breath test within a pre-defined timeout period, such as ten, twenty or thirty minutes.

In one variation of the above-described process, the breath analysis application 62 may notify the user when a determination is made to perform a predictive sensor heating operation. This notification may inform the user that the breath analysis device 30 is being prepared for use or may prompt the user to indicate whether the breath analysis device 30 should be prepared for use. If the user indicates that the breath analysis device should not be prepared for use, the sensor heating operation is postponed, or is aborted if already started.

In another variation, when the sensor heating operation is predictively performed, the sensor 38 may be heated to a temperature falling below the necessary or target temperature for performing the breath test. If the user then proceeds with performing the breath test, the sensor is further heated until it reaches the target temperature. With this variation, the heating delay ordinarily encountered by the user is reduced but is not completely avoided. For example, the predictive heating operation may be performed such that the delay encountered by the user is reduced by over 80% (e.g., the user encounters a ten second delay rather than the usual two-minute delay).

FIG. 2 illustrates one embodiment of a process that may be implemented by the breath analysis application 62, and more specifically its predictive heating logic 64, to determine whether to predictively initiate a sensor heating operation. In this particular embodiment, one or more measurement time windows are used. The measurement time windows may, for example, be based on a predefined time schedule (e.g., 6 AM to 9 AM daily and 9 PM to 11 PM daily), or may be based on particular events (e.g., six to eight hours after most recent breath test). As mentioned above, the illustrated logic and process may alternatively be implemented without the use of time windows. In addition, the illustrated process may alternatively be implemented partly or wholly in executable code executed by the server 70, the breath analysis device 30, or another processing node.

In block 100 of FIG. 2, the process initially waits for the start of a measurement time window. Once the window has started, the process checks, in block 102, to determine whether one or more conditions are met for performing a predictive heating operation (and/or other sensor or device preparation operation). In some embodiments, the only condition that is checked is whether a wireless (e.g., Bluetooth) link is, or can be, established between the smartphone 50 and the breath analysis device 30. If such a link can be established, the user is assumed to be in the same location as the breath analysis device 30.

Depending upon the types of sensor-based data, if any, available, the process in some embodiments may additionally or alternatively require one or more of the following conditions (among others) to be satisfied in block 102: (1) the smartphone 50 is at a predefined location, such as a home or work location, at which the user ordinarily performs breath tests; these locations may, for example, be prespecified by the user via a configuration UI of the breath analysis app 62 and/or may be learned automatically by the system based on the user's usage pattern; (2) the user is awake, as may be determined or inferred based on data collected/reported by a smartwatch, sleep monitoring device, or other user-worn accessory 80, and/or based on whether the user has recently used, or is currently using, the smartphone 50; (3) the speed at which the smartphone 50 is moving falls below a defined threshold, such as five or ten miles per hour, as may be determined based on GPS coordinates of the smartphone over a defined time period (e.g., the preceding five minutes); (4) the user's heart rate, as may be measured and reported by a smartwatch or other user-worn accessory 80, falls below a defined threshold, such as 70 or 80 beats per minute; (5) a voice call is not currently in progress on the smartphone 50; (6) the user's breathing rate, as may be measured and reported by a smartwatch or other user-worn accessory 80, falls below a defined threshold; (7) the user's skin temperature, as may be measured and reported by a smartwatch or other user-worn accessory 80, falls below a defined threshold. All combinations of the foregoing conditions fall within the scope of this disclosure, and various other conditions may be checked in some embodiments. The determination made in block 102 constitutes a prediction of whether the user is in an adequate state for performing a breath test.

In some embodiments of block 102, the process may generate a multi-factor score based on some or all of the foregoing factors or conditions and may compare this score with a threshold to determine whether to initiate the sensor preparation operation. In generating the score different amounts of weight may be given to different factors or conditions.

As further illustrated in FIG. 2, the determination of block 102 may be made repeatedly until either the time window expires (see block 104) or the condition(s) for predictively initiating a heating operation is/are met. If the time window expires, the breath analysis application 62 may output an appropriate notification to the user (block 106). For example, a notification may be displayed reminding the user to perform a breath test when conditions are appropriate. When a positive determination is made in block 102 of FIG. 2, the breath analysis application 62 causes the smartphone 50 to transmit a command to the breath analysis device 30 to perform sensor heating operation (block 108). The sensor heating operation thus occurs without the need for the user to interact with (e.g., turn on) the breath analysis device, interact with the breath analysis app 62, or indicate a desire to perform a breath test.

The process may then wait to receive a "heating complete" or "device ready" message from the breath analysis device 30 (block 110), and then generate a notification to the user indicating that the breath analysis device is ready for use (block 112). In some embodiments, the breath analysis device 30 may also output a visual, audible and/or haptic signal at this point to notify the user that it is ready for use. The process then waits until either a breath test is performed or a time-out period expires (block 114) before turning off the MOS sensor's heating element to allow the sensor to cool, and then loops back to wait for the start of the next time window. (In some embodiments, the MOS sensor 38 may be further heated after the breath test before allowing it to cool, as may be desirable for preparing the sensor for its next use.) The timeout period may, for example, be twenty, thirty or forty minutes.

Preferably, the user can also initiate a breath test at any time (e.g., by depressing a button on the breath analysis device 30 or via the breath analysis application 62), even if the MOS sensor 38 has not been predictively heated. In such cases, however, the user typically must wait a few minutes for the MOS sensor to be heated.

In one embodiment, the process of FIG. 2 is modified such that the smartphone 50 automatically attempts to connect to the breath analysis device 30 and initiate the sensor heating/preparation operation at the start of the time window. In this embodiment, block 102 is omitted. If the attempt to connect is unsuccessful, the smartphone may periodically retry the connection/initiation operation for a defined time period, such as for the duration of the time window.

As mentioned above, the process of FIG. 2 may alternatively be performed partly or wholly by a device other than the smartphone. For example, in one embodiment, the breath analysis device 30 makes the determination of whether to predictively perform a sensor heating operation; this determination may, for example, be made based solely on the current time, or based on the current time and whether the breath analysis device 30 is within Bluetooth range of the smartphone 50. This determination may also be based on data received from the smartphone 50 regarding the user's physical activity.

As will be appreciated, the above-described processes are also applicable to breath analysis devices that use other types of analyte sensors for which one or more sensor preparation tasks are performed, including but not limited to electrochemical, colorimetric, piezoelectric, gravimetric and optical sensors.

Embodiments with Docking Station

As mentioned above, in some embodiments the breath analysis device 30 may be configured to be placed into a docking station or cradle 120 (FIGS. 3 and 4) that charges the battery 44 of the breath analysis device. In these embodiments, the docking station 120 may include a wireless transceiver, such as a WIFI or Bluetooth transceiver, that supplements, or takes the place of, the wireless transceiver 42 of the breath analysis device. The docking station 120 may also include an electrical interface that enables a processor of the docking station to communicate with the processor 40 of the breath analysis device 30 when the device 30 is docked.

In one such embodiment, the smartphone 50 communicates wirelessly with the docking station 120, both to determine whether the breath analysis device 30 is docked and to initiate sensor heating/preparation operations. For example, when the smartphone 50 determines that a sensor heating operation should predictively be performed, it may send a command to the docking station 120, which may respond by effectively passing this command via the electrical interface to the breath analysis device 30. The docking station 120 may itself be a smart device that makes programmatic determinations of when or whether to initiate sensor preparation operations.

In the embodiment shown in FIGS. 3 and 4, the breath analysis device 30 can be inserted into the docking station 120 in two orientations, a charging orientation (FIG. 3) and a mouthpiece sterilization orientation (FIG. 4). In the charging orientation, the distal end of the breath analysis device 30 extends into the docking station 120, and the docking station charges the rechargeable battery 44 of the breath analysis device through electrical contacts or through a magnetic charging interface. In the mouthpiece sterilization orientation, the mouthpiece 122 inserts into the docking station 120, and the docking station emits UV light that sterilizes the mouthpiece. In one variation, the orientation shown in FIG. 4 functions as both a charging and sterilization orientation.

In the embodiment shown in FIGS. 3 and 4, the docking station or cradle 120 includes a sensor 124, such as a light sensor, sound sensor, and/or odor sensor, capable of detecting a condition that can be used as a trigger (e.g., a bedroom light being turned on, the sound of a baby crying, the sound of a person talking, or the smell of coffee). The output of this sensor 124 may be used as a trigger for initiating a sensor heating or other sensor preparation cycle. For example, the system may be configured such that the detection of one of the aforesaid conditions between 5 AM and 8 AM causes the breath analysis device's sensor preparation operation to be initiated. Although the docking station 120 is shown in FIGS. 3 and 4 as being A/C powered, it may alternatively be powered by another type of power source (DC, solar, etc.).

Embodiments with No Smartphone

In some embodiments, the system may be implemented without a smartphone 50 or other mobile computing device. In such embodiments, the logic or program code for determining whether to predictively initiate a sensor heating or preparation operation may exist solely in the breath analysis device 30, and/or in an associated docking station 120 as described above. In these embodiments, the breath analysis device 30 (or an associated docking station 120) may initiate a sensor heating operation based solely on the time of day, or based on multiple factors as described above.

The breath analysis device 30 (or docking station 120) may additionally or alternatively initiate sensor heating/preparation based on one or more types of triggering events. For example, the breath analysis device 30 (or docking station) may be configured as an IoT (Internet of things) device capable of communicating with one or more other IoT devices or systems in the user's home, such as a home security system, a motion detector, a refrigerator, a bathroom scale, a coffee maker, etc. The sensor heating or preparation operation may then be based on such triggering events as the user returning home, getting out of bed in the morning, turning on the lights, using the bathroom scale, using a kitchen appliance, etc. In yet another embodiment, the breath analysis device 30 is configured as an IoT device capable of responding to triggering events as described above, but is also capable of being used in conjunction with a mobile application as described herein. In yet another embodiment, the sensor heating or preparation operation may be initiated in response to a determination or prediction that the user is about to wake up, as may be assessed based, e.g., on data from a patient-worn or other sleep monitoring device (e.g., data indicating completion of stage 4 REM sleep), and/or blood glucose or blood ketone levels monitored by a continuous monitoring device.

Figure 5:
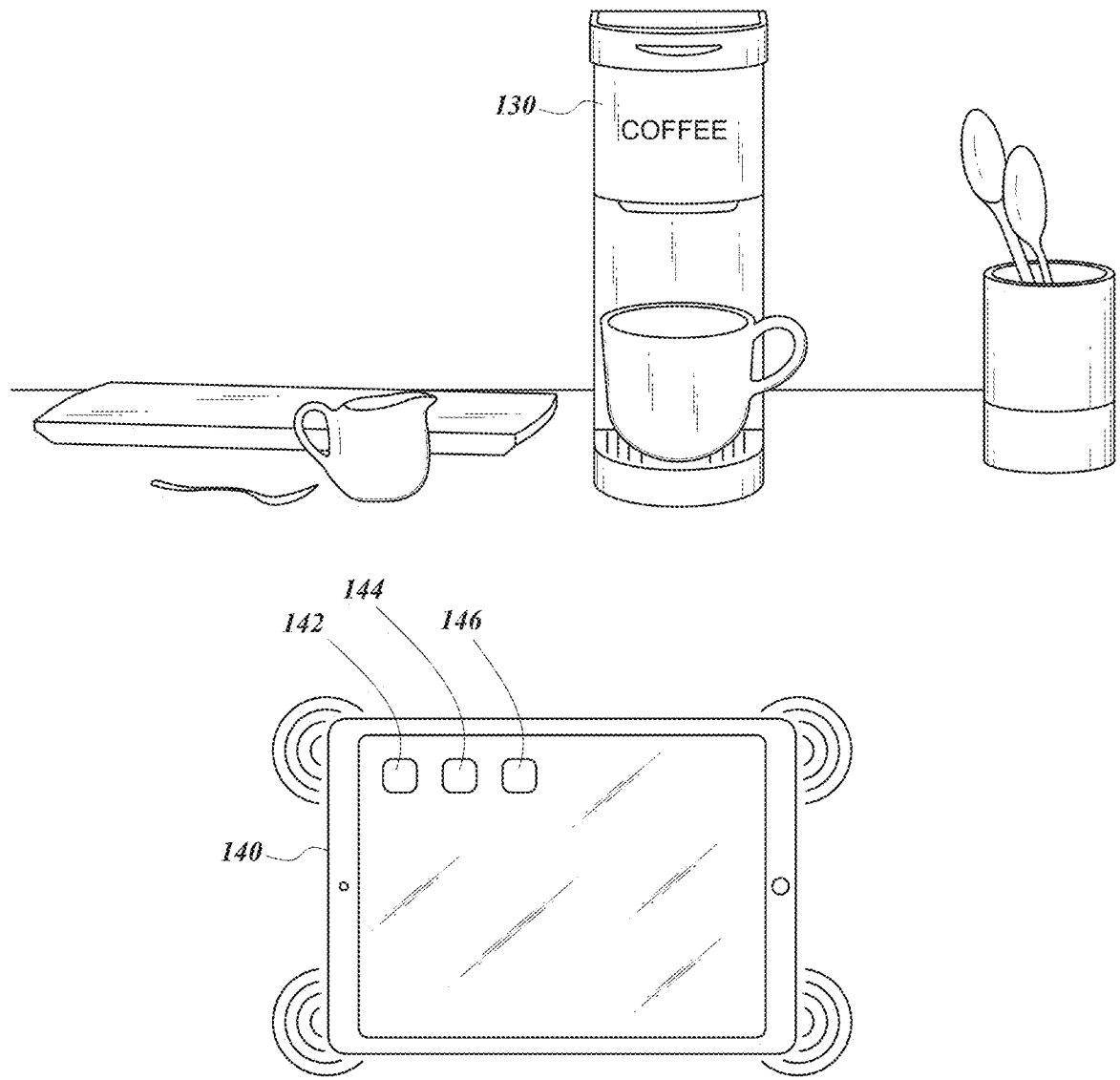
FIG. 5 illustrates an environment in which the use of a coffee machine can serve as a trigger for initiating the preparation of a breath analysis device.

FIG. 5 illustrates an example environment in which use of a coffee maker 130 can serve as a trigger for initiating sensor preparation. The coffee maker 130 may be an IoT device that emits a wireless signal when in use. Alternatively, an external device, such as a docking station 120 or Alexa-enabled device, may be configured to detect the sound emitted by the coffee maker 130 when coffee is being brewed. In either case, if use of the coffee maker 130 is detected during a defined time window (e.g., 6 AM to 9 AM), the system may instruct the breath analysis device 30 to initiate a sensor preparation operation as described above.

FIG. 5 also shows a tablet computing device 140 (e.g., iPad) that may optionally be included in the environment. In the illustrated environment, the tablet 140 is shared by multiple users (e.g., family members of co-workers) that participate in a health monitoring program, and displays a respective icon 142, 144, 146) for each such user. These users may share a single breath analysis device 30 or may each use their own respective breath analysis device 30. The illustrated icons can be selected on the tablet to view the breath measurements or scores of the respective users and to access a UI for specifying time windows and/or other conditions or parameters for initiating sensor preparation operations. The tablet 140 may alternatively be another type of feedback system capable of displaying information from multiple people.

Conclusion

The various tasks described herein, such as the determinations of when or whether to initiate sensor heating or preparation tasks, may be performed or controlled by execution of program instructions by one or more hardware processors. The program instructions may be stored in a computer-readable storage medium, such as a non-volatile solid-state memory. The tasks may alternatively be performed by application-specific circuitry, such as an ASIC (Application Specific Integrated Circuit). As mentioned above, although this disclosure focuses on the initiation of a sensor heating operation, it is also applicable to any other type of preparation task that is performed to prepare a breath analysis device or sensor(s) thereof for use.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

Although this invention has been described in terms of certain embodiments and applications, other embodiments and applications that are apparent to those of ordinary skill in the art, including embodiments which do not provide all of the features and advantages set forth herein, are also within the scope of this invention. Accordingly, the scope of the present invention is intended to be defined only by reference to the claims.

What is claimed is:

1. A portable breath analysis system, comprising:
    a battery powered breath analysis device comprising a breath input port coupled to a breath flow path, a semiconductor analyte sensor positioned along the breath flow path, a wireless transceiver, and a processor, said breath analysis device configured to perform a sensor heating operation to prepare the semiconductor analyte sensor for use, and to use the semiconductor analyte sensor to measure a concentration of an analyte in a breath sample received through the breath input port; and
    a mobile application configured to run on a smartphone of a user and to communicate wirelessly with the breath analysis device;
    wherein the mobile application is configured to (1) predict whether the user is in an adequate state for performing a breath test in which the user exhales the breath sample into the breath analysis device, and (2) in response to predicting that the user is in said adequate state for performing the breath test, initiate wireless transmission to the breath analysis device of a command that causes the breath analysis device to predictively perform said sensor heating operation in preparation for said breath test;

whereby the system reduces or avoids a user-perceived delay associated with the sensor heating operation.

2. The portable breath analysis system of claim 1, wherein the mobile application predicts whether the user is in said adequate state based at least partly on global positioning system (GPS) data indicative of a current location of the smartphone.

3. The portable breath analysis system of claim 1, wherein the mobile application predicts whether the user is in said adequate state based at least partly on data reflective of a current proximity of the smartphone to the breath analysis device.

4. The portable breath analysis system of claim 1, wherein the mobile application predicts whether the user is in said adequate state based at least partly on sensor data reflective of whether the user is awake.

5. The portable breath analysis system of claim 1, wherein the mobile application predicts whether the user is in said adequate state based at least partly on heart rate data.

6. The portable breath analysis system of claim 1, wherein the mobile application predicts whether the user is in said adequate state based at least partly on sensor data reflective of whether the smartphone is in motion.

7. The portable breath analysis system of claim 1, wherein the mobile application predicts whether the user is in said adequate state based at least partly on a current time.

8. The portable breath analysis system of claim 1, wherein the breath analysis device periodically wakes up the wireless transceiver according to a duty cycle in which the wireless transceiver is maintained in a low-power state most of the time.

9. The portable breath analysis system of claim 1, wherein the mobile application is responsive to completion of the sensor heating operation by providing a notification to the user.

10. A method of preparing a breath analysis device for use, the method comprising:
programmatically predicting whether a user is in an adequate state for performing a breath test in which the user exhales into the breath analysis device; and
in response to predicting that the user is in an adequate state for performing the breath test, initiating a sensor preparation operation in which a semiconductor analyte sensor of the breath analysis device is prepared for use in said breath test in which the user exhales into the breath analysis device, such that a user-perceived delay associated with the sensor preparation operation is avoided or reduced;
said method performed under control of program instructions executed by one or more processors.

11. The method of claim 10, wherein programmatically predicting whether the user is in said adequate state comprises determining whether the breath analysis device is within wireless communication range of a smartphone associated with the breath analysis device.

12. The method of claim 10, wherein programmatically predicting whether the user is in said adequate state comprises using global positioning system (GPS) data to determine a current location of a smartphone associated with the user.

13. The method of claim 10, wherein programmatically predicting whether the user is in said adequate state comprises analyzing data reflective of a physiologic state of the user.

14. The method of claim 13, wherein the data reflective of a physiologic state of the user comprises heart rate data.

15. The method of claim 13, wherein the data reflective of a physiologic state of the user comprises breathing rate data.

16. The method of claim 10, wherein programmatically predicting whether the user is in said adequate state comprises determining, based on sensor data, whether the user is awake.

17. The method of claim 10, wherein programmatically predicting whether the user is in said adequate state comprises determining, based on sensor data, a rate of motion of a smartphone associated with the breath analysis device.

18. The method of claim 10, wherein programmatically predicting whether the user is in said adequate state comprises determining whether a current time of day coincides with a scheduled time for performing the breath test.

19. The method of claim 10, wherein the sensor preparation operation comprises a sensor heating operation.

20. The method of claim 10, wherein the program instructions are executed by a processor of a smartphone associated with the breath analysis device.

21. A portable breath analysis system, comprising:
a battery powered breath analysis device comprising a breath input port coupled to a breath flow path, and a semiconductor sensor positioned along the breath flow path, said breath analysis device configured to perform a sensor preparation operation to prepare the semiconductor sensor for use, and to use the semiconductor sensor to measure a concentration of an analyte in a breath sample received through the breath input port; and
a hardware processor configured to (1) predict whether a user of the breath analysis device is ready to perform a breath test in which the user exhales the breath sample into the breath analysis device, and (2) in response to predicting that the user is ready to perform the breath test, initiate the sensor preparation operation to prepare the semiconductor sensor for use in said breath test;
whereby the system reduces or avoids a user-perceived delay associated with the sensor preparation operation.

22. The system of claim 21, wherein the sensor preparation operation comprises a sensor heating operation.

23. The system of claim 21, wherein the processor is configured to predict whether the user is ready to perform the breath test based at least partly on data reflective of a location of the user.

24. The system of claim 21, wherein the processor is configured to predict whether the user is ready to perform the breath test based at least partly on data reflective of a proximity of the breath analysis device to a smartphone associated with the breath analysis device.

25. The system of claim 21, wherein the processor is configured to predict whether the user is ready to perform the breath test based at least partly on data reflective of a physiologic state of the user.

26. The system of claim 21, wherein the processor is configured to predict whether the user is ready to perform the breath test based at least partly on a current time of day.

27. The system of claim 21, wherein the processor is configured to predict whether the user is ready to perform the breath test based at least partly on an output of a sound sensor.

* * * * *